United States Patent [19]

van Eijk

[11] Patent Number: Plant 7,239

[45] Date of Patent: May 29, 1990

[54] IRIS PLANT NAMED TOKYO

[75] Inventor: Joseph P. van Eijk, Ve Bennekom, Netherlands

[73] Assignees: H.J.A. Rooyakkers B.V.; World Flower B.V., both of Netherlands

[21] Appl. No.: 336,004

[22] Filed: Apr. 10, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Iris plant named Tokyo having relatively dark violet blue flower color, large plant size and sturdy growth habit, and excellent flower production. The limbs of the outer petals or falls are formed with a median band or stripe bright yellow-orange in color and providing an attractive contrast to the dark violet blue flower color.

1 Drawing Sheet

1

The present invention comprises a new and distinct cultivar of iris plant, botanically known as *Iris tingitana,* and commonly known as Dutch Iris. The new cultivar is named Tokyo.

The new cultivar was originated from a cross made by applicant in a controlled breeding program in Wageningen, The Netherlands. The female, or seed, parent was an unnamed *Iris tingitana* cultivar having blue with purple flowers. The male, or pollen, parent was likewise an unnamed *Iris tingitana* cultivar having dark blue flowers.

Tokyo was discovered and selected by applicant as a flowering plant within the progeny of the stated cross in a controlled environment in Wageningen, The Netherlands. Asexual reproduction of the new cultivar by division of rhizomes, as performed by applicant at the Institute for Horticultural Plant Breeding, Wageningen, The Netherlands, has demonstrated that the combination of characteristics as herein disclosed for the new cultivar are firmly fixed and retained through successive generations of asexual reproduction.

Tokyo has not been observed under all possible environmental conditions. The phenotype may vary significantly with variations in environment such as temperature, light intensity and day length. The following observations, measurements and values describe the new cultivar as grown in Breezand, The Netherlands under conditions which closely approximate those generally used in commercial practice.

The following traits have been repeatedly observed and are determined to be basis characteristics of Tokyo which in combination distinguish this Iris as a new and distinct cultivar:

1. Relatively dark violet blue flower color.
2. Plant is relatively large and sturdy.
3. Good flower production capabilities.
4. The bulbs are elongated rather than round.
5. In the limb of each outer petal or fall, a central band or stripe of bright yellow orange extends from the claw to approximately one-third the length of the limb, with the band having an irregular, light violet blue border.

The new cultivar is similar to known and commercially available Dutch irises with respect to plant and flower shape. However, Tokyo is unique due to its flower color, large plant size, and flower production capabilities.

2

The accompanying photographic drawing shows a typical bud, a flower, and leaves of a specimen plant of the new cultivar. The colors appearing in the photograph are as true as possible with color illustrations of this type.

In the following description, color references are made to the Royal Horticultural Society Colour Chart (R.H.S.), except where general colors of ordinary significance are referred to. Color values were taken under natural light conditions approximately 12 noon in Hillegom, The Netherlands.

Botanical classification: *Iris tingitana* c.v. Tokyo.

Parentage:

*Male parent.*—An unnamed *Iris tingitana* (dark blue).

*Female parent.*—An unnamed *Iris tingitana* having flowers which are blue with purple.

Propagation: The new cultivar holds its distinguishing characteristics through successive propagations by division of rhizomes.

Plant:

*Growth.*—Can exceed 1.1 meter in height in May--June.

*Form.*—Upright, erect and well rounded.

*Stems.*—Straight, dark green in color.

*Foliage.*—Long, tapering, tip acute, dark green in color.

Flowers:

*Buds.*—Size: 7 cm in length. Opening: Normal. Color: Green with dark blue stripe. Spathe: Normal.

*Bloom.*—Size of Entire Bloom: 13 cm in diameter. Form of Entire Bloom: Generally triangular. Shape and Color of Outer Petals: The outer petals or falls are oblong with the claw somewhat tapering and having a white upper surface with purple veins, a border approximately 90B, and a central stripe or band approximately 17C. The limb is round, convex, and curves downwardly perpendicular to the claw, with the edges being wavy and crenate; color approximately 90A with darker veins, with a central band or stripe 17A extending approximately ⅓ of the length of the limb, with the band or stripe having an irregular border surrounded by light violet 92B. On the underside, the claw is approximately 83B with a band or stripe 154B; limb is approximately 90A, with a similar band or stripe of 8A, surrounded by a somewhat lighter violet. Shape and Color of Inner Petals: The limbs are narrow, elliptic, concave, with the edges wavy and slightly crenate; inner and outer surfaces approximately 90A, with narrow, barely visible yellow stripes appearing on the inside of the petals at the base. Keeping Qualities: Very good. Fragrance: Barely scented. Beard: Border somewhat wrinkled and irregularly crenate; upper surface approximately 92A, under surface slightly lighter with white veins.

Reproduction organs: The stamens with filaments are approximately as long as the anther and are yellow at the base, and white with a hint of purple elsewhere; anther, light yellow, and pollen yellow; pistil is leaf-shaped, bridge curved outward, convex, oblong and broadening; there is a band or median on the upper surface with a very narrow dark purple ridge, with bordering being a lighter purple 86B extending through a band 78A and blending into a thin mauve somewhat transparent border; undersurface similar.

I claim:

1. A new and distinct cultivar of Iris plant named Tokyo, as illustrated and described.

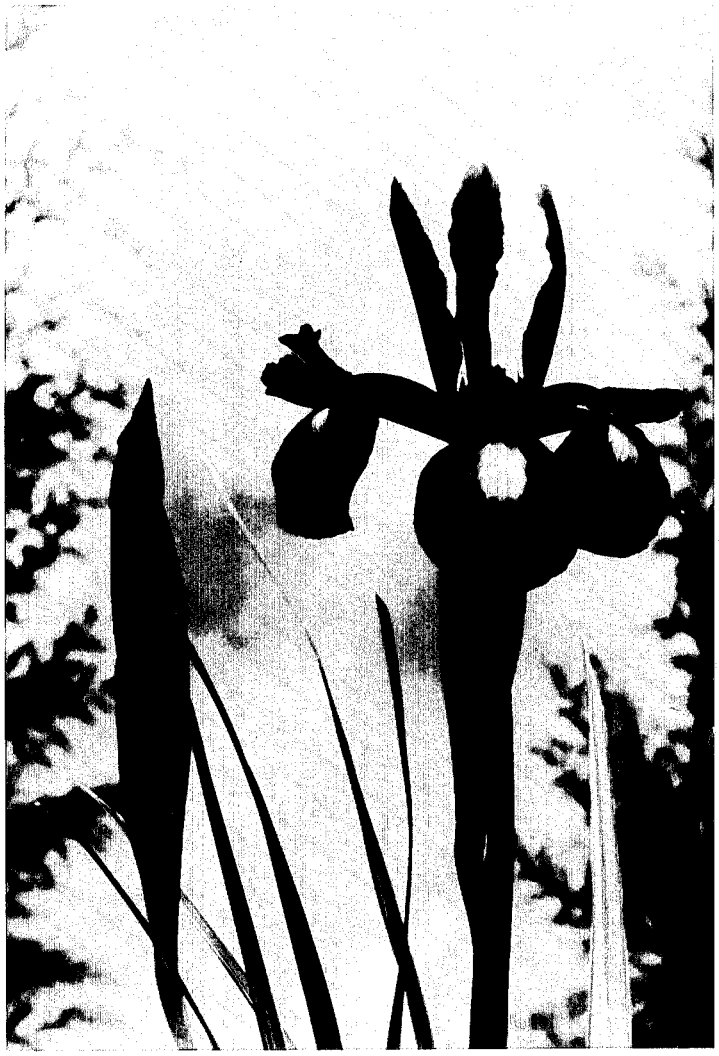

* * * * *